US009944900B2

(12) United States Patent
Gage

(10) Patent No.: US 9,944,900 B2
(45) Date of Patent: Apr. 17, 2018

(54) PULSATILE PERFUSION EXTRACTION METHOD FOR NON-EMBRYONIC PLURIPOTENT STEM CELLS

(75) Inventor: Fred Gage, Kensington, MD (US)

(73) Assignee: Hemacell Perfusion, Silver Spring, MD (US)

( * ) Notice: Subject to any disclaimer, the term of this patent is extended or adjusted under 35 U.S.C. 154(b) by 330 days.

(21) Appl. No.: 11/654,553

(22) Filed: Jan. 18, 2007

(65) Prior Publication Data

US 2007/0190649 A1 Aug. 16, 2007

Related U.S. Application Data

(60) Provisional application No. 60/759,556, filed on Jan. 18, 2006.

(51) Int. Cl.

| | |
|---|---|
| ***C12N 5/0789*** | (2010.01) |
| ***A61L 27/36*** | (2006.01) |
| ***A61L 27/38*** | (2006.01) |
| ***A61L 27/50*** | (2006.01) |
| ***C12N 5/073*** | (2010.01) |
| ***A01N 1/02*** | (2006.01) |

(52) U.S. Cl.

CPC ........... *C12N 5/0647* (2013.01); *A01N 1/021* (2013.01); *A01N 1/0236* (2013.01); *A01N 1/0247* (2013.01); *A01N 1/0289* (2013.01); *A61L 27/3683* (2013.01); *A61L 27/3834* (2013.01); *A61L 27/507* (2013.01); *C12N 5/0605* (2013.01)

(58) Field of Classification Search

CPC .... A01N 1/021; A01N 1/0236; A01N 1/0247; A01N 1/0289; A61L 27/3683; A61L 27/3834; A61L 27/507; C12N 5/0605; C12N 5/0647

USPC .......................................................... 435/378

See application file for complete search history.

(56) References Cited

U.S. PATENT DOCUMENTS

| | | | | |
|---|---|---|---|---|
| 3,632,473 A | 1/1972 | Belzer et al. | | |
| 3,862,002 A | 1/1975 | Sanders | | |
| 4,065,264 A | 12/1977 | Lewin | | |
| 5,752,929 A | 5/1998 | Klatz et al. | | |
| 6,461,645 B1 | 10/2002 | Boyse et al. | | |
| 6,632,651 B1 * | 10/2003 | Nevo et al. | 435/286.5 | |
| 6,811,965 B2 | 11/2004 | Vodovotz et al. | | |
| 6,953,655 B1 | 10/2005 | Hassanein | | |
| 6,977,140 B1 | 12/2005 | Owen et al. | | |
| 7,011,623 B2 | 3/2006 | Clerin et al. | | |
| 7,014,990 B2 | 3/2006 | Polyak et al. | | |
| 7,045,148 B2 | 5/2006 | Hariri | | |
| 7,060,494 B2 | 6/2006 | Bhat | | |
| 7,255,879 B2 | 8/2007 | Hariri | | |
| 7,311,904 B2 | 12/2007 | Hariri | | |
| 7,468,276 B2 * | 12/2008 | Hariri | 435/325 | |
| 7,504,201 B2 * | 3/2009 | Taylor | A01N 1/02 | 435/1.2 |
| 8,057,788 B2 | 11/2011 | Hariri | | |
| 8,329,468 B2 | 12/2012 | Takebe | | |
| 2003/0032179 A1 | 2/2003 | Hariri | | |
| 2003/0180269 A1 | 9/2003 | Hariri | | |
| 2004/0219136 A1 | 11/2004 | Hariri | | |
| 2005/0032209 A1 | 2/2005 | Messina et al. | | |
| 2005/0037491 A1 | 2/2005 | Mistry et al. | | |
| 2005/0272148 A1 | 12/2005 | Hariri | | |
| 2006/0153816 A1 | 7/2006 | Brown et al. | | |
| 2006/0153818 A1 | 7/2006 | Dhanaraj et al. | | |
| 2006/0154367 A1 | 7/2006 | Kihm et al. | | |
| 2006/0182724 A1 | 8/2006 | Riordan | | |
| 2007/0190649 A1 | 8/2007 | Gage | | |
| 2008/0131410 A1 | 6/2008 | Hariri | | |

FOREIGN PATENT DOCUMENTS

| | | |
|---|---|---|
| CN | 1548529 | 11/2004 |
| WO | WO02064755 | 8/2002 |
| WO | WO03068937 | 8/2003 |
| WO | 2005001081 A1 | 1/2005 |
| WO | WO2007047468 | 4/2007 |
| WO | WO2007078183 | 7/2007 |

OTHER PUBLICATIONS

Leeser et al., 2004, Transplantation Proceedings 36:1050-1051.*
Bornstein et al., 2005, Stem Cells 23:324-334.*
Peng et al., 2000, Am. J. Physiol. Cell. Physiol. 279:C797-C805.*
Dougherty, F.C. et al., "Characterization of Perfusion Pump Performance Using Harmonic Analysis", Bioengineering Conference, ASME 2001, BED—vol. 50, 2001.
Addison, et al., "Metabolism of Prednisolone by the Isolated Perfused Human Placental Lobule", J. Steroid Biochem. Molec. Biol. vol. 39, No. 1, pp. 83-90, 1991.
Matsuoka, et al., "Pulsatile Perfusion Reduces the Incidence of Delayed Graft Function in Expandd Criteria Donor Kidney Transplantation", American Journal of Transplantation, 2006, 6, pp. 1473-1478.
Hammon, John W., "Extracorporeal Circulation: Perfusion System", Cardiac Surgery in the Adult. New York: McGraw-Hill, 2008, pp. 350-370 Chapter 12A.
Murkin, et al., "Cardiopulmonary Bypass, Myocardial Management and Support Techniques: A Randomized Study of the Influence of Perfusion Technique and pH Management Strategy in 316 Patients Undergoing Coronary Artery Bypass Surgery: II. Neurologic and Cognitive Outcomes", J. Thorac Cardiocasc Surg 1995, 110, pp. 349-362.

(Continued)

*Primary Examiner* — Christopher M Babic
*Assistant Examiner* — Kelaginamane T Hiriyanna
(74) *Attorney, Agent, or Firm* — Mendelsohn Dunleavy, P.C.

(57) ABSTRACT

A method for extracting stem cells from a non-embryonic stem cell source, including providing a non-embryonic stem cell source including stem cells; perfusing the non-embryonic stem cell source with a pulsatile flow of a perfusion solution to produce a perfusate including stem cells and a perfused non-embryonic stem cell source; and isolating the stem cells from the perfusate to produce isolated stem cells, is provided. Also provided is a non-embryonic stem cell line derived from a non-embryonic stem cell obtained using the pulsatile perfusion extraction method.

8 Claims, 8 Drawing Sheets

(56) References Cited

OTHER PUBLICATIONS

Thompson, et al., "The Influence of Pulsatile and Nonpulsatile Extracorporeal Circulation on Fluid Retention Following Coronary Artery Bypass Grafting", Perfusion 1992, 7, pp. 201-211.
Belvedere, et al., "Increased Blood Volume and CD34+CD38- Progenitor Cell Recovery Using a Novel Unbilical Cord Blood Collection System", Stem Cells, 2000, 18, pp. 245-251.
Moore, et al., "A Simple Perfusion Technique for Isolation of Maternal Intervillous Blood Mononuclear Cells from Human Placentae", Journal of Immunological Methods, 1997, vol. 209, pp. 93-104.
Davis, et al., "Maximal Cord Blood Recovery and CD34+ Progenitor Cell Collection Using Machine Pulsatile Perfusion of Placentas", Blood (ASH Annual Meeting Abstracts) 2006, 108: Abstract 3643, American Society of Hematology.
Ameida Proada—Formation of Human—Blood—2004—104—p. 2582-2590.
Azisa—Engraftment and migration—Proc Natl Acad 1998 p. 3908-3913.
Barker—Searching for unrelated donor—Biol Blood Marrow Tr. 2002—p. 257-260.
Bertolini—Comparative study of differnt—J Hematother—Feb. 1995—4—p. 29-36.
Bessems—Improved Rat Liver Preservation—Liver Transplantation, v 11-5—May 2005—p. 539-546.
Bhattacharya—Direct Identification—Invest Ophthalmol Vis Sci v 44 Jun. 2003 p. 2764-2773.
Bicknese—Human umbilical cord blood—Cell Transplant 11—2002—p. 261-264.
Brazelton—From marrow to brain—Science 190—2000 p. 1775-1779.
Cai—In search of stemness—Inter Soc for Exp Hematology—Elsevier 32—2004 p. 585-598.
Cai—Membrane properties of rat—J Neurochem 2004—88—p. 212-226.
Cai—Properties of a fetal multipotent—Dev Biol 251—2002 p. 221-240.
Camargo—Hematopoietic myelomonocytic—J Clin Invest 113—2004—p. 1266-1271.
Chen—Human Umbilical Cord Blood—Stem Cells—Ohio—2005 p. 1560-1571.
Cogle—Bone marrow transdifferentiation—Lancet 363—2004—p. 1432-1437.
Conneally—Expansion in Vitro of transplantable—Proceedings of Nat Aca Sci USA—v 94—18—1997—p. 9836-9841.
Corti—Transplanted ALDH—Hum Mol Genet 15—2006—p. 167-187.
Donaldson—Impact of obstetric factors—Br J of Haematology 106—1999—p. 128-129.
Eglitis—Hematopoietic cells—Proc Natl Acad Sci USA 94—1997—p. 1080-1085.
Escolar—Transplantation of umbilical-cord—N Engl J Med 352—2005—p. 2069-2087.
Ferrari—Muscle regeneration by bone marrow-derived—Science 279—1998—p. 1528-1530.
Forraz—Characterization of a lineage-negative—Stem cells 22—2004—p. 100-108.
Fortunel—Comment on Sternness—Science 302—5 pages.
Gage—A Comparison study of the Belzer—Transplant Proc 29—1997—p. 3643.
Gekas—The Placenta is a niche for hematopoietic—Dev Cell 8—2005—p. 365-375.
George—Factors associated with parameters of engraftment—Transplantation and Cellular Engineering—v 46—Oct 2006—13 pages.
Gluckman—Outcome of cord-blood transplantation—Eurocord Transplant Grp—337—6—p. 373-381.
Goodwin—Multilineage differentiation activity—Biol Blood Marrow Transplant 7—2001—3 pages.
Harris—Collection separation and cryopreservation—Bone Marrow transplantation 13—1994—p. 135-143.
Hruban—Fluorescence in situ—Am J Pathol 142—1993—p. 975-980.
Jaatinen—Global Gene Expression Profile—Stem Cells 24—2006—p. 631-641.
Kim—The multidrug resistance transporter—Clin Cancer Res 8—2002—p. 22-28.
Korbling—Hepatocytes and epithelial—N Engl J Med 346—2002—p. 738-746.
Kuci—Identification of a novel class—Blood 101—2003—p. 869-876.
Kucia—Morphological and molecular—Leukemia 21—2007—p. 297-300.
Kurtzberg—Placental Blood as a Source—N Eng J Med 335—1996—p. 157-166 + Correction 1997—3 pages.
Lagassi—Purified hematopoietic stem cells—Nat Med 6—2000—p. 1229-1234.
Lasky—In ugtero or ex utero cord—Transfusion 42—2002—3 pages.
Laughlin—Ourcomes after transplantation—N Engl J Med 351—2004—p. 2265-2275.
McGuckin—Production of stem cells—Cell Prolif 38—2005—4 pages.
McGuckin—Umbilical cord blood stem—Exp Cell Res 295—2004—p. 350-359.
Mezey—Turning blood into brain—Science 290—2000—p. 1779-1782.
Migishima—Full reconstitution of hematopoietic—Transplantation 75—2003—p. 1820-1826.
Muller—Cardiomyocytes of noncardiac—Circulation 106—2002—p. 31-35.
Okamoto—Damaged epithelia regenerated—Nat Med 8—2002—p. 1011-1017.
Ottersbach—The murine placenta contians hematopoietic—Dev Cell 8—2005—p. 377-387.
Parmar—Sca+CD34—murine side—Exp Hematol 31—2003—p. 244-250.
Parolini—Concise Review Isolation—Stem Cells 26—2008—p. 300-311.
Petersen—Bone marrow as a potential—Science 284—1999—p. 1168-1170.
Quaini—Chimerism of the traqnsplanted heart—N. Engl J. Med 346—2002—p. 5-15.
Rubinstein—Outcomes among 562 recipients—N. Engl J. Med 339—1998—p. 1565-1577.
Rubinstein—Storec placental blood—Blood 81—1993—p. 1679-1690.
Sanchez-Ramos—Adult bone marrow stromal—Exp Neurol 164—p. 247-256. Year 2000.
Sanchez-Ramos—Expression of neutral markers—Exp Neurol 171—2001—p. 109-115.
Sanchez-Ramos—Natural cells derived from adult bone—Exp Neurol 69—2002—p. 880-883.
Scharenberg—the ABCG2 transporter—Blood 99—2002—p. 507-512.
Shlebak—the impact of antenatal and perinatal—Br J Haematol 103—1998—3 pages.
Storms—Isolation of primitive human—Proc Natl Acad Sci USA 96—1999—p. 9118-9123.
Takebe—Preliminary Findings on the use of Pulsatile—Transfusion—v 49—9—Sep. 2009—p. 1911-1916.
Takebe—Generation of dual resistance—Mol Ther 3—2001—p. 88-96.
Takebe—Methotrexate selection—Cancer Gene Ther 9—2001 p. 308-320.
Theise—Liver from bone marrow in humans—Hepatology 32—2000—p. 11-16.
Turner—A modified harvest technique—Bone marrow transplantation—1992—2 pages.
Wagner—Successful transplantation of HLA—Blood 88—1996—p. 795-802.

(56) References Cited

OTHER PUBLICATIONS

Wagner—Transplantation of unrelated donor—Blood 100—2002—p. 1611-1618.
Wagner—Umbilical cord and placental blood—J. Hematother 1—1992—p. 167-173.
Wang—Albumin-expressing hepatocyte-like—Blood 101—2003—p. 4201-4208.
Wang—Cell fusion is the principal source—Nature 422—2003—p. 897-901.
Zhou—The ABC transporter Bcrp—Nat Med 7—2001—p. 1028-1034.
Zigava—Human umbilical cord blood—Cell Transplant 11—2002—p. 265-274.
Complete file history of U.S. Appl. No. 12/530,236 Sep. 8, filed 2009.

* cited by examiner

PULSATILE PERFUSION EXTRACTION METHOD FOR NON-EMBRYONIC PLURIPOTENT STEM CELLS

BACKGROUND OF THE INVENTION

Embryonic stem cells, such as mesenchymal stem cells, are generally considered the most desirable type of pluripotent cells useful for research and therapeutic use. However, there are religious and ethical objections to the use of embryonic stem cells, and federal funding of research utilizing embryonic stem cells has been restricted to cells from 14 embryonic cell lines. Some researchers fear one or more of the federally approved embryonic stem cell lines may become contaminated or non-viable.

In response, researchers have sought non-embryonic stem cell sources. Umbilical cord and placenta are believed to be rich sources of stem cells. See Dhot et al., "Cord blood stem cell banking and transplantation," *Indian J. Pediatr.* 70:989-992 (2003) and "Umbilical Cord Matrix, a rich new stem cell source, study shows," *Life Science News* (Jan. 16, 2005).

An advantage of harvesting umbilical cord and placenta for stem cells is that a far greater number of stem cells can be recovered from the umbilical cord and placenta than from an embryo. More particularly, only about 30 to 35 stem cells can be obtained per embryo. In comparison, about 10.1+/−1.2 $10^8$ stem cells can be extracted from an umbilical cord, and about 7.1+/−0.8 $10^8$ stem cells can be extracted from a placenta, including the umbilical cord. Barney, "The daily interview: the market opportunity for stem cell research," TheStreet.com (Aug. 6, 2001).

Umbilical cord and placental stem cells can also be cultured to grow more stem cells after cryopreservation. Liu et al., "Cryobiological characteristics of placental cord blood preserved in bioarchive auto-preserved liquid nitrogen system," *Zhongguo Shi Yan Xue Ye Xue Za Zhi.,* 10:261-264 (2002).

There are at least two methods typically used to obtain stem cells from the umbilical cord or placenta. The first method involves simply draining blood from the placenta and/or umbilical cord into a closed sterile collection bag using gravity. Solves et al., "Comparison between two strategies for umbilical cord blood collection," *Bone Marrow Transplant.* 31:269-273 (2003). Other researchers have used pressure to extract blood from the umbilical cord and/or placenta. See, for example, Romanov et al., "Searching for alternative sources of postnatal human mesenchymal stem cells: candidate MSC-like cells from umbilical cord," *Stem Cells* 21:105-110 (2003) (Umbilical cord vein cannulated on both sides, washed with Earle's balanced salt solution, and then gently "massaged" to collect a suspension of endothelial and subendothelial cells).

An important potential use for umbilical and placental stem cells is for unrelated bone marrow donor/recipient transplantation. Stevens et al., "Placental/umbilical cord blood for unrelated-donor bone marrow reconstitution: relevance of nucleated red blood cells," *Blood,* 100:2662-2664 (2002). However, the yield from the umbilical cord is only sufficient for pediatric transplantation. When researchers attempted to transplant umbilical cord stem cells into adults, the procedure was unsuccessful due to insufficient stem cell yields.

Perfusion science seeks to maintain an organ's natural function using mechanical means. Perfusion has been mostly utilized in cardiac-thoracic surgery, vascular surgery, and preservation of organs for transplantation. See, for example, U.S. Pat. No. 6,811,965.

At least one researcher has flushed the placenta with perfusate through the arterial-vein circuit to eliminate tissue residual blood, Zhang et al., "Human placenta-derived mesenchymal progenitor cells support culture expansion of long-term culture-initiating cells from cord blood CD34+ cells," *Exp Hematol.* 32:657-664 (2004). However, there have been no reported extractions of cord blood from either an umbilical cord or a placenta using pulsatile perfusion.

There are significant differences between pulsatile perfusion of the placenta and non-pulsatile perfusion, which can include the following:

1. pulsatile perfusion mimics the action of the heart, thus allowing for a smooth transition from the mother to the perfusion circuit;

2. pulsatile perfusion has been shown to vasodilate the vascular structure of organs and also vasodilates the placental vascular structure;

3. pulsatile perfusion increases the osmotic pressure of the perfusion solution, thus more efficiently removing the placental blood from the interior of the placental cells;

4. in pulsatile perfusion one typically adjusts the perfusate chemistries, pH, $PCO_2$ and $PO_2$, to duplicate normal body chemistries, thus extracting placental blood without causing any detrimental effects, such as renewed vasoconstriction of the vascular structure;

5. pulsatile perfusion is less harmful to the endothelial cells of the vascular structure, thus allowing placental arteries and vein to be used for human vascular allografts.

An object of this invention is to provide an improved method for obtaining pluripotent stem cells without destroying an embryo. Another object of this invention is to provide a method for obtaining pluripotent stem cells in sufficient yield to permit unrelated adult bone marrow transplants of such pluripotent stem cells.

A feature of this invention is the use of pulsatile perfusion to extract stem cells from a non-embryonic source.

An advantage of this invention is the extraction of up to twice as many stem cells from a placenta or umbilical cord than that achieved by simply draining these organs.

SUMMARY OF THE INVENTION

A method for extracting stem cells from a non-embryonic stem cell source is provided and can comprise or consist of providing a non-embryonic stem cell source comprising stem cells; perfusing the non-embryonic stem cell source with a pulsatile flow of a perfusion solution to produce a perfusate comprising stem cells and a perfused non-embryonic stem cell source; and isolating the stem cells from the perfusate to produce isolated stem cells.

Also provided is a method for extracting stem cells from a non-embryonic source that can comprise or consist of placing a non-embryonic source of stem cells into a perfusion circuit; extracting the stem cells from said non-embryonic source by pulsatile perfusion to produce a perfusate; and isolating the stem cells from the perfusate.

Provided is a method for producing a non-embryonic stem cell line, that can comprise or consist of culturing the isolated stem cells in stem cell culture media to produce the non-embryonic stem cell line.

Also provided is a method for producing a vascular tissue graft that can comprise or consist of collecting the perfused non-embryonic stem cell source; and isolating arteries and/or veins from the perfused non-embryonic stem cell source to produce the vascular tissue graft.

DETAILED DESCRIPTION OF THE EMBODIMENTS

Figure 1:
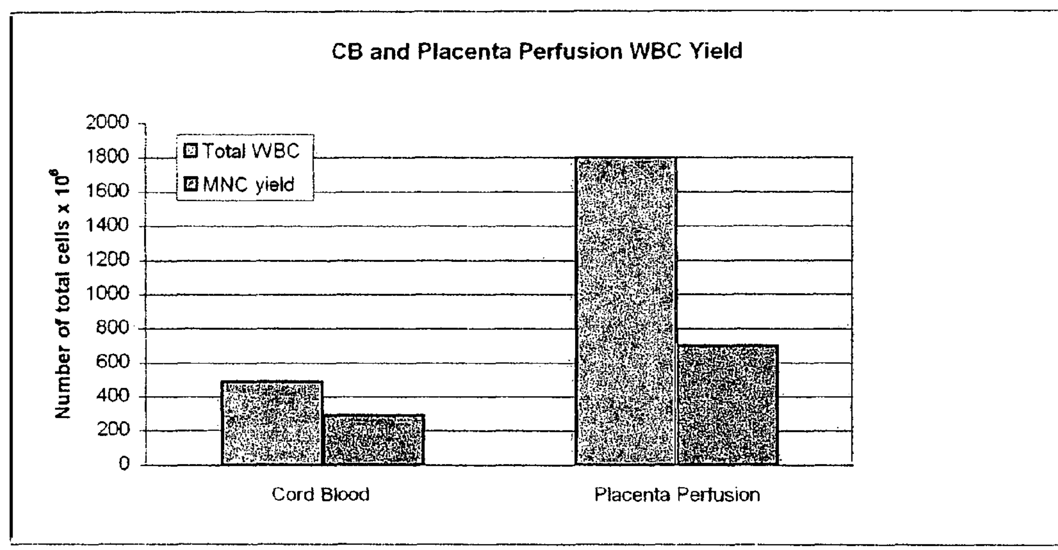
FIG. 1 is a graph which plots the total number of blood cells vs. white blood cell yield contained in a cord blood sample extracted by syringe prior to umbilical cord/placenta perfusion according to the method of the present invention.

The term "effective amount" means concentrations or amounts of components which are effective for producing an intended result.

The term "non-embryonic stem cell source" means any non-embryonic tissue source that can comprise stem cells. Suitable non-embryonic stem cell sources can comprise placenta and/or umbilical cord.

The term "perfusate" means the fluid that has been caused to flow over and/or through an organ, tissue or lumen.

The term "perfusion circuit" means a circuit for delivering a perfusion solution from a reservoir to a non-embryonic stem cell source to be perfused. The perfusion circuit can comprise a pulsatile perfusion machine that can comprise a pulsatile perfusion pump adapted to pump a perfusion solution through an organ or tissue, and a storage compartment to collect the perfusate. The pulsatile perfusion pump can comprise a centrifical perfusion pump, a roller perfusion pump, or a mechanical pulsatile perfusion pump.

The term "perfuse" or "perfusion" means the act of causing a fluid to flow over and/or through an organ, tissue, or lumen. For example, to cause a fluid to flow from an artery through the vascular bed of a tissue, for example, placenta and/or umbilical cord.

The term "perfusion solution" means any buffered physiological solution that can comprise a salt solution or a cell culture media.

The term "pulsatile flow" means the rhythmic, intermittent propagation of a fluid through a tissue or vessel or system, in contrast to smooth propagation, which produces laminar flow.

The non-embryonic stem cell source can comprise an umbilical cord and/or placenta. The umbilical cord may be clamped or tied off after a child is delivered. Preferably, an effective amount of an anticoagulant such as heparin and/or warfarin sodium can be administered to the non-embryonic stem cell source, for example, the placental arteries. The anticoagulant can be administered in an amount effective to prevent dot formation. An illustrative example is a bolus of 10,0000 units of heparin administered, for example, as 5,000 units into each artery. The placenta/umbilical cord is then finished being delivered and placed into 3 sterile isolation bags, with each isolation bag being individually tied shut. The packaged placenta/umbilical cord can be cooled to approximately 0° C. to 4° C., or to 0° C., prior to perfusion. For example, the placenta/umbilical cord may be placed into a Styrofoam ice chest with wet ice to await delivery to a perfusion laboratory.

The present method can employ any conventional pulsatile perfusion machine. The construction and operation of such pulsatile perfusion machines is well known to those of ordinary skill in the art. See U.S. Pat. Nos. 3,632,473; 4,065,264; and 5,752,929; the disclosures of each of which are hereby incorporated by reference herein. Such machines can comprise a perfusion circuit having a storage compartment and a pulsatile perfusion pump adapted to pump a perfusion solution through an organ. The pulsatile perfusion pump can comprise a centrifical perfusion pump, a roller perfusion pump, or a mechanical pulsatile perfusion pump.

In the present method, the perfusion machine is adapted to pump a perfusion solution through a non-embryonic stem cell source and into its storage compartment or reservoir to collect the perfusate, which will contain materials extracted from the non-embryonic stem cell source, for example, cord and/or placental blood comprising stem cells.

The perfusion solution can comprise one or more of a colloidal agent, an anti-edema agent, an antioxidant, an anti-inflammatory agent and a vasodilator. The perfusion solution can comprise a colloidal agent, an anti-edema agent, an antioxidant, an anti-inflammatory agent and a vasodilator. The perfusion solution can comprise one or more additional additives, for example, comprising oxygenation agents such as perfluorocarbons; pH buffering agents such as HEPES; and other additives such as hormones, steroids, antimicrobial agents such as penicillin, magnesia, and/or insulin.

The colloidal agent serves to effectively remove blood from the umbilical cord and/or placenta. Hydroxyethyl starch is a preferred colloidal agent.

The anti-edema agent serves to prevent cell swelling, and can be present in an amount sufficient to maintain the osmotic pressure of the solution. The osmotic concentration of the perfusion solution ("osmolarity") can be in a range of from about 300 to about 400 mOsmols of solute/liter of solution, or from about 310 to about 350 mOsmols of solute/liter of solution. The perfusion solution can have a pH temperature, corrected to 37° C., within a range of from 7.35 to 7.45. Suitable anti-edema agents can comprise one or more sugars, for example, comprising sucrose, dextrose, raffinose, lactobionate, gluconate and mannitol.

The antioxidant can be present in an amount sufficient to prevent oxidation of the stem cells, and can comprise glutathione or allopurinol. Other antioxidants which may be added to the perfusion solution can comprise vitamins A, B, C and E, selenium, cysteine, BHT and BHA.

The anti-inflammatory agent can be present in the perfusion solution in an amount effective to prevent inflammation of the non-embryonic stem cell source, for example, umbilical cord and/or placenta. A suitable antinflammatory agent is dexamethasone.

The vasodilator can be present in an amount effective to dilate the arteries of the non-embryonic stem cell source, for example, umbilical cord and/or placenta. The vasodilator can comprise one or more of adenosine and nitric oxide.

Suitable perfusion solutions are well known to those of ordinary skill and many are commercially available. Suitable perfusion solutions can comprise or consist of any physiological solution, for example, a salt solution, and/or a cell culture media. Suitable perfusion solutions can comprise or consist of one or more of the following: BES, BIS-TRIS, BIS-TRIS propane, EPPS, Gly-Gly, HEPES, HEPES sodium salts, MES hydrate, MES sodium salts, MOPS, MOPS sodium salts, PIPES, TAPS, TAPS sodium salts, TAPSO TES, Tricine, Trizma® base, Trizma® Hydrochloride, Trizma® hydrochloride buffer solution, Trizma® Preset crystals, Alsever's Solution, Ames Medium, Basal Medium Eagle, Click's Medium, Dulbecco's Modified Eagle's Medium-high glucose, Dulbecco's Modified Eagle's Medium-low glucose, Dulbecco's Modified Eagle's Medium/Nutrient Mixture F-12 Ham, Dulbecco's Phosphate Buffered Saline, Earle's Balanced Salts, Gey's Balanced Salt Solution, Glasgow Minimum Essential Medium, Grace's Insect Medium, Hanks' Balanced Salt Solution, IPL-41 Insect Medium, Iscove's Modified Dulbecco's Medium, Iscove Modified Dulbecco's Medium, Krebs-Henseleit Buffer Modified, Krebs-Ringer bicarbonate buffer, L-15 Medium (Leibovitz), McCoy's 5A Medium, MCDB 105 Medium, MCDB 110 Medium, MCDB 131 Medium, MCDB 153 Medium, MCDB 201 Medium, Medium 199, Mega Cell™ Dulbecco's Modified Eagle's Medium, Mega Cell™ Dulbecco's Modified Eagles Medium/Nutrient Mixture F-12 Ham, Mega Cell™ Minimum Essential Medium Eagle, Mega Cell™ Minimum Essential Medium/Nutrient Mixture F-12 Ham, Mega Cell™ RPMI-1640 Medium, Minimum Essential Medium Eagle, NCTC 109 medium, Nutrient Mixture F-10 Ham, Nutrient Mixture F-12 Ham, RPMI 1640, RPMI 1640 Medium with L-glutamine and sodium bicarbonate, RPMI 1640 HEPES Modification with 25 mM HEPES without L-glutamine, RPMI-1640 medium Modified with 20 mM Hepes and L-glutamine and sodium bicarbonate, RPMI 1640 Medium with sodium bicarbonate without L-glutamine, RPMI 1640 Medium Dutch Modification with sodium bicarbonate and 20 mM HEPES without L-glutamine, RPMI 1640 medium 10X without glutamine folic acid and sodium bicarbonate, RPMI 1640 medium modified with sodium bicarbonate without methione, cystine and L-glutamine, RPMI 1640 medium modified with sodium bicarbonate without L-glutamine and phenol red, RPMI 1640 medium HEPES modification, with L-glutamine 25 mM HEPES without sodium bicarbonate, RPMI 1640 medium with L-glutamine without glucose and sodium bicarbonate, RPMI 1640 medium modified with L-glutamine without phenol red and sodium bicarbonate, RPMI 1640 medium powder, AutoMod™ cell cultured tested, Schneider's insect medium, Shields and Sang M3 insect medium, TC-100 insect medium, TNM-FH insect medium, Tyrode's salts, Waymouth MB 752/1 medium, Williams' medium E, Hanks, Eagles, Albumin, Belzer Machine perfusion solution or generic versions, Celsior or generic versions, Euro-Collins or generic Versions, HTK or generic versions, Lactated Ringers or generic versions, Plasmanate or generic versions, Hespan or generic versions, Normal Saline or generic versions, IGL or generic versions, Vasosol or generic versions, and/or Viaspan or generic versions.

The non-embryonic source of stem cells, typically a placenta and/or umbilical cord, is placed into a sterile, dosed perfusion circuit, typically by cannulating the placenta and/or umbilical cord using an appropriate sized, sterile stainless steel or plastic, for example Teflon® polytetrafluoroethylene, cannula which is preferably sized from 2 mm to 5 mm, and silk ties (0, 1, 2, 3), or umbilical tape. After being placed in the perfusion circuit, the placental vein or umbilical cord is opened to allow the placental blood to be perfused out of the placenta and/or umbilical cord.

Pulsatile perfusion is begun by starting the perfusion pump, which can be operated so as to produce a systolic perfusion pressure in a range of from about 50 to about 150 mmHg, or from about 90 mmHg to about 120 mmHg. The pulsatile perfusion circuit can be operated at a temperature in the range of from about 4° C. to about 40° C., or from about 15° C. to about 20° C. Pulsatile perfusion avoids undesirable vasospasm of the arterial-vein circuit.

Pulsatile perfusing can be carried out under conditions that simulate conditions of the non-embryonic stem cell source in vivo. For example, the pulsatile perfusion machine can be operated to simulate conditions of the non-embryonic stem cell source in vivo. Such conditions can comprise or consist of one or more of systolic pressure, temperature, pulse rate, and diastolic pressure. For example, when perfusing a placenta and umbilical cord, a suitable pulse rate can comprise from 60 beats per minute to 80 beats per minute, or 70 beats per minute; and at a systolic perfusion pressure in a range of from about 50 to about 150 mmHg, or from about 90 mmHg to about 120 mmHg, or about 100 mmHg.

Pulsatile perfusion can be carried out for an amount of time sufficient to collect stem cells from the non-embryonic stem cell source. For example, perfusion can be carried out for a time period of from about 5 minutes to about 1 hour, for about 10 minutes to about 30 minutes, for about 15 minutes to about 25 minutes, or for about 20 minutes.

In an embodiment, the perfusion machine pump is primed with a priming solution prior to pulsatile perfusion of the non-embryonic source. The priming solution and the perfusion solution can be the same solution.

The placenta/umbilical cord may be discarded as biohazardous trash after the placental blood has been perfused out of the placenta and/or umbilical cord and into the perfusion circuit's storage compartment. Alternatively, any perfused vessels can be further processed, for example, decellularized and/or preserved and/or repopulated, to produce a vascular tissue graft, for example, a vascular allograft or xenograft, for use in a patient.

Cord blood is heavier than the perfusion solution and thus can easily be separated from the perfusate. The stem cells can be isolated from the other cord blood components using techniques and apparatus well known to those of ordinary skill in the art, such as centrifugation, density gradient centrifugation, cell sorting, flow cytometry, magnet cell separation, affinity cell separation, or differential adhesion techniques. For example, the stem cells may be isolated by centrifugation using a COBB® 2991 Blood Cell Processor (Gambro BCT, Inc.) to separate the stem cells and white blood cells from red blood cells, plasma and platelets, and then washed, for example with Normal Saline or Lactated Ringer's solution (or Ficolls solution).

As discussed above, a centrifugation process can be used to remove the original perfusate solution from the placental blood. Typically, this process also removes plasma, platelets and red cells leaving the stem cells and white blood cells. However, if a patient would prefer to have any of these blood components the centrifugation process can be modified to alter the cells that are removed from the perfusate, for example, in the wash cycle of the COBE 2991 cell sorter system. A preferred range for the centrifugation process is to spin the collected perfusate for a time in the range of from 7 to 20 minutes at a centrifuge speed of from 500 to 3,000 revolutions per minute (RPM) to separate the perfusion solution, platelets, plasma, and red cells; or for a time in the range of from 10 to 12 minutes at a centrifuge speed of from 1,000 to 1,200 RPM. After the first centrifugation step, Ficoll Solution can be added as a preservative system to preserve the stem cells, for example, before starting the cryopreservation process. From 250 ml to 500 ml of Ficoll Solution may preferably be added to the remaining stem cells by gravity and then the centrifugation system can be set to run at a speed in the range of from 2,000 to 5,000 RPM, from 2,500 to 3,500 RPM, for a time in the range of from 15 to 30 minutes, or for about 20 minutes. When this process has ended a sample of the stem cells (1 micro liter) can be placed in a flow cytometer to quantify the total number of stem cells that were recovered, and to determine stem cell purity and viability. The stem cells can then be transferred into appropriate sized containers for distribution and may either be stored at 4° C. in a refrigerator for immediate use or cryopresserved at −180° C. and stored in vapor phase liquid nitrogen. Each storage vial or container can be bar coded for identification before storage.

Whether the isolated stem cells are used immediately or cryopreserved for later use, a sample of the placental blood may be used to identify the human lymphocyte antigens (HLA) of the stem cells and the blood type of the stem cells.

The stem cells obtained by the present method can be used to create a cell line by placing them in a tissue culture medium which contains appropriate nutrients and permitting the cells to grow. Suitable culturing conditions include agar media for the cells to grow different types of colonies (General, Erythroid colonies, Granulopoietic colonies, Multi-linage colonies, Megakaryocyte colonies, Blast colonies, Polycythemia Vera Colonies (PV), Chronic Myeloid Leukemia Colonies (CML), Myelodysplastic Syndromes (MDS) and Acute Myeloid Leukemia (AML) Colonies. In order to grow colonies the appropriate culture media will be used and then the stem cells will be placed into a $CO_2$ incubator at an established temperature and humidity. Set forth below are two illustrative $CO_2$ tissue culture media:

| Methylcellulose Medium containing Agar LCM* | |
|---|---|
| Methycellulose | 0.9% |
| Fetal Bovine Serum | 30% |
| Bovine Serum Albumin | 1% |
| 2-Mercaptoethanol | 10-4M |
| Agar Leukocyte Conditioned Medium | 10% |
| Erythropoietin | 3 nits/ml |
| Iscove's DMEN (N,N-dimethylethylenediamine) | 60% |
| Methylcellulose Medium | |
| Methylcellulose | 0.9% |
| Fetal Bovine Serum | 30% |
| Bovine Serum Albumin | 1% |
| 2-Mercaptoethanol | 10-4M |
| L-Glutamine | 2 mM |
| Stem Cell Factor' | 5O ng/ml |
| Granulocytes Macrophage-CSF | IO ng/ml |
| Interleukin-3 | IO ng/ml |
| Erythropoetin | 3 units/ml |
| Iscove's DMEN (N,N-dimethylethylenediamine) | 70% |

*Formulas taken from "Atlas of Human Hematopoietic Colonies" Published by Stem cell Technologies, Inc.

Stem Cell Factor (SCF) is a hematopoietic growth factor that exerts its activity at the early stages of hematopoiesis. SCE stimulates the proliferation of myeloid, erythroid, and lymphoid progenitors in bone marrow cultures and has been shown to act synergistically with colony stimulating factors. Recombinant human SCF is an 18.4 kDa protein containing 164 amino acid residues corresponding to the soluble secreted form of SCF.

EXAMPLES

The following Examples illustrate in even greater detail specific embodiments of the invention. These Examples are intended to illustrate the practice and advantages of the invention, and are not intended to limit the allowable scope of the invention in any manner whatsoever.

Example 1

Extraction of Stem Cells by Pulsatile Perfusion of Baboon Placenta

An obstetrician obtained a 50 ml sample of blood from the umbilical cord by syringe during delivery of an infant baboon by cesarean section.

The placenta was then placed into the organ chamber of a RM3 Kidney Perfusion System (Waters Medical Systems, Rochester, Minn.), and the placenta arteries were cannulated using with a 3 mm, straight cannula manufactured by Waters Medical Systems. The cannulas were tied in place with 0-Silk ties. Prior to perfusion, the perfusion circuit was primed with a perfusion solution comprising RPMI 1640 with Gluconate Tissue Media and 10,000 units of heparin.

Pulsatile perfusion was commenced using the same perfusion solution. The systolic pressure was set at 100 mm Hg with a pulse rate of 70 beats per minute at room temperature. After 20 minutes of pulsatile perfusion, the perfusate was transferred from the perfusion circuit into a sterile container and both the perfusate and the 50 cc cord blood sample were analyzed by flow cytometry for CD-34+ cells. The perfused placenta yielded over twice as many stem cells as the blood sample. See Table 1.

TABLE 1

| Comparison of Stem Cell Yields from Perfuse Baboon Placenta and Umbilical Cord Blood | |
|---|---|
| Perfused Baboon Placenta | $3.34 \times 10^8$ cells |
| Baboon Umbilical Cord Blood | $1.6 \times 10^8$ cells |

Example 2

Pulsatile Perfusion of Human Placenta

Informed consent was obtained from an expectant human female prior to delivery. Approximately 37 cc of cord blood was extracted by syringe from the unbilical cord after delivery of the infant but prior to expulsion of the placenta. The placenta and umbilical cord were obtained from the female shortly after delivery. The placenta was placed into the organ chamber of a RM3 Kidney Perfusion System, and perfused in accordance with the procedures and conditions of Example 1, except that Belzers Machine Perfusion Solution was used in place of the perfusion solution (RPMI 1640 with Gluconate Tissue Solution) used therein.

The 37 cc blood sample and the perfusate were analyzed by flow cytometry. Test data is set forth below in Tables 2-6, which are graphically shown in FIGS. 1-5.

Figure 2:
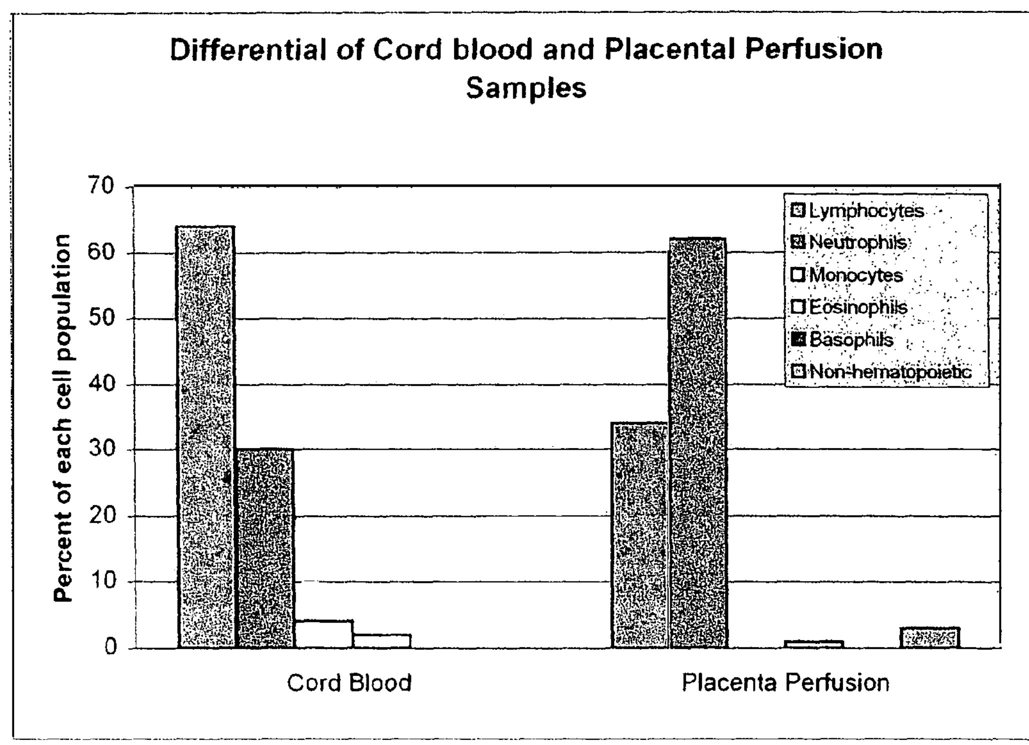
FIG. 2 is a graph which plots the percentage of cell population vs. cell yield by type of cell contained in a cord blood sample extracted by syringe prior to umbilical cord/placenta perfusion according to the method of the present invention.

Table 2 and FIG. 1 demonstrate that perfusion of the umbilical cord/placenta can extract a significant amount of white blood cells, while Table 3 and FIG. 2 illustrate that there is significant similarity between the cord blood sample extracted by syringe and the blood sample collected by perfusion of the umbilical cord/placenta.

TABLE 2

| Total Number of Cells × $10^6$ | | |
|---|---|---|
| | Cord Blood Syringe Sample | Placenta Perfusion |
| Total White Blood Cells | 488 | 1800 |
| Mononuclear Cell Yield | 289.2 | 700 |

TABLE 3

| Sample Differential (Percentage) | | |
|---|---|---|
| | Cord Blood Syringe Sample | Placenta Perfusion |
| Lymphocytes | 64 | 34 |
| Neutrophils | 30 | 62 |
| Monocytes | 4 | 0 |
| Eosinophils | 2 | 1 |
| Basophils | 0 | 0 |
| Non-hematopoietic | 0 | 3 |

Figure 3:
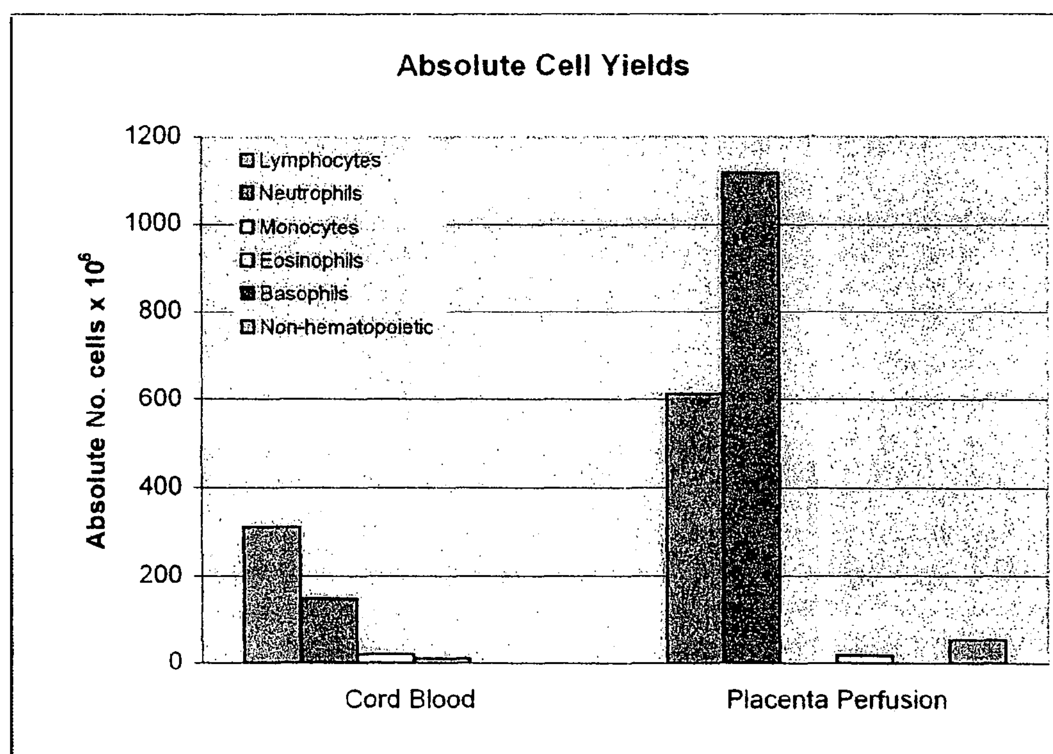
FIG. 3 is a graph which plots the absolute number of cells vs. cell yield by type of cell contained in a cord blood sample extracted by syringe prior to umbilical cord/placenta perfusion according to the method of the present invention.

Table 4 and FIG. 3 show the significant increase in the number of cells collected by perfusion of the umbilical cord/placenta in comparison to the number of cells in the 37 cc sample collected by syringe prior to perfusion.

TABLE 4

| Total Number of Cells × $10^6$ | | |
|---|---|---|
| | Cord Blood Syringe Sample | Placenta Perfusion |
| Lymphocytes | 312 | 612 |
| Neutrophils | 146.4 | 1116 |
| Monocytes | 19.52 | 0 |
| Eosinophils | 9.76 | 18 |
| Basophils | 0 | 0 |
| Non-hematopoietic | 0 | 54 |

Figure 4A:
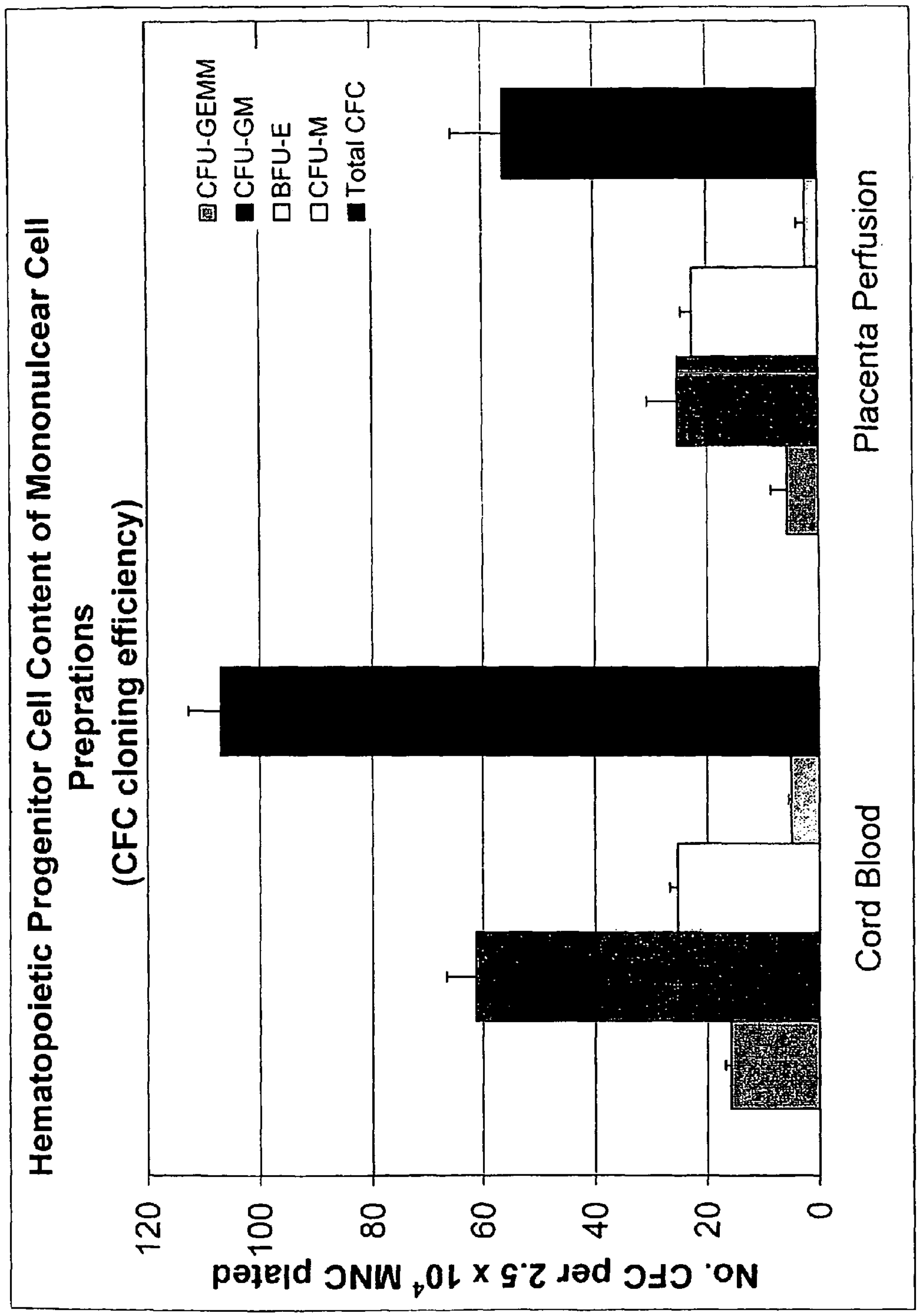
FIG. 4A is a graph which plots the cloning efficiency achieved from a mononuclear cell preparation derived from a syringe cord blood sample and an umbilical cord/placenta perfusate sample.

Table 5A and FIG. 4A illustrate the cloning efficiency achieved derived from a mononuclear cell preparation of the cord blood sample and a mononuclear cell preparation of the umbilical cord/placenta perfusate. The cord blood sample achieved higher number of colonies than the umbilical cord/placenta perfusate in all number of colony types.

TABLE 5A

| Cloning Efficiency-Mononuclear Cell Preparation (mean number of colonies per 2.5 × $10^4$ cells plated) | | | | |
|---|---|---|---|---|
| Colony Type | Cord Blood | Placenta Perfusion | SD1 | SD2 |
| CFU-GEMM | 15.9 | 5.7 | 0.88 | 2.9 |
| CFU-GM | 61.3 | 25.33 | 5.5 | 5.37 |
| BFU-E | 25.33 | 22.6 | 1.45 | 2.02 |
| CFU-M | 5 | 2.3 | 0.57 | 1.5 |
| Total CFC | 107 | 56 | 5.6 | 9.6 |

CFU-GEMM means "Colony Forming Units—Granulocytes, Erythroid Macrophage, Megarkaryocites"—colonies which produce 20 or more cells including some from at least the first 2 types named.

CFU-GM means "Colony Forming Units—Granulocytes Macrophage"—colonies which produce at least 20 granulocytes and macrophages.

CFU-E means "Colony Forming Units—Erythroid"—colonies which produce 8-200 erthroblasts in 1-2 clusters.

CFU-M means "Colony Forming Units—Macrophages"—colonies which produce at least 20 macrophages.

BFU-E means "Burst Forming Unit—Erythroid"—produces three or more clusters of erythroblast or an equivalent number of erythroblasts.

CFC means "Colony Forming Unit Cultures"—the total number of all colony and burst forming units.

Figure 4B:
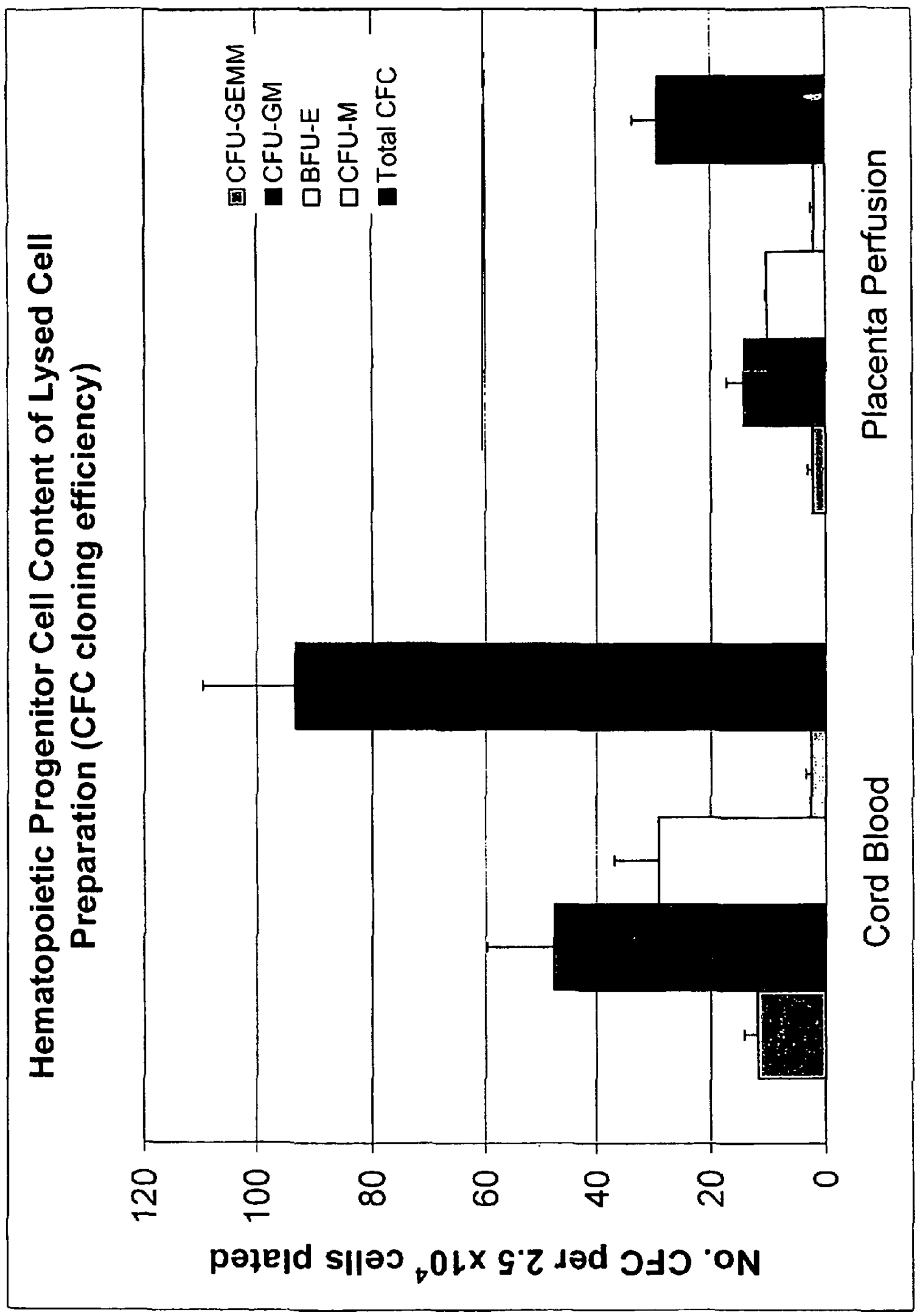
FIG. 4B is a graph which plots the cloning efficiency achieved from a lysed cell preparation derived from a syringe cord blood sample and an umbilical cord/placenta perfusate sample.

Table 5B and FIG. 4B report the cloning efficiency achieved using a lysed cell preparation in which all red cells have been removed derived from a syringe cord blood sample and an umbilical cord/placenta perfusate sample. The cord blood sample achieved higher number of colonies than the umbilical cord/placenta perfusate in all number of colony types.

TABLE 5B

| Cloning Efficiency-Lysed White Blood Cell Preparation (mean number of colonies per 2.5 × $10^4$ cells plated) | | | | |
|---|---|---|---|---|
| Colony Type | Cord Blood | Placenta Perfusion | SD1 | SD2 |
| CFU-GEMM | 12 | 2.33 | 2.3 | 0.88 |
| CFU-GM | 47.6 | 14.3 | 12.1 | 2.9 |
| CFU-E | 29 | 10.3 | 7.8 | 0.33 |
| CFU-M | 2.7 | 2 | 0.88 | 0.58 |
| Total CFC | 93.33 | 29 | 16.2 | 4.36 |

Figure 4C:
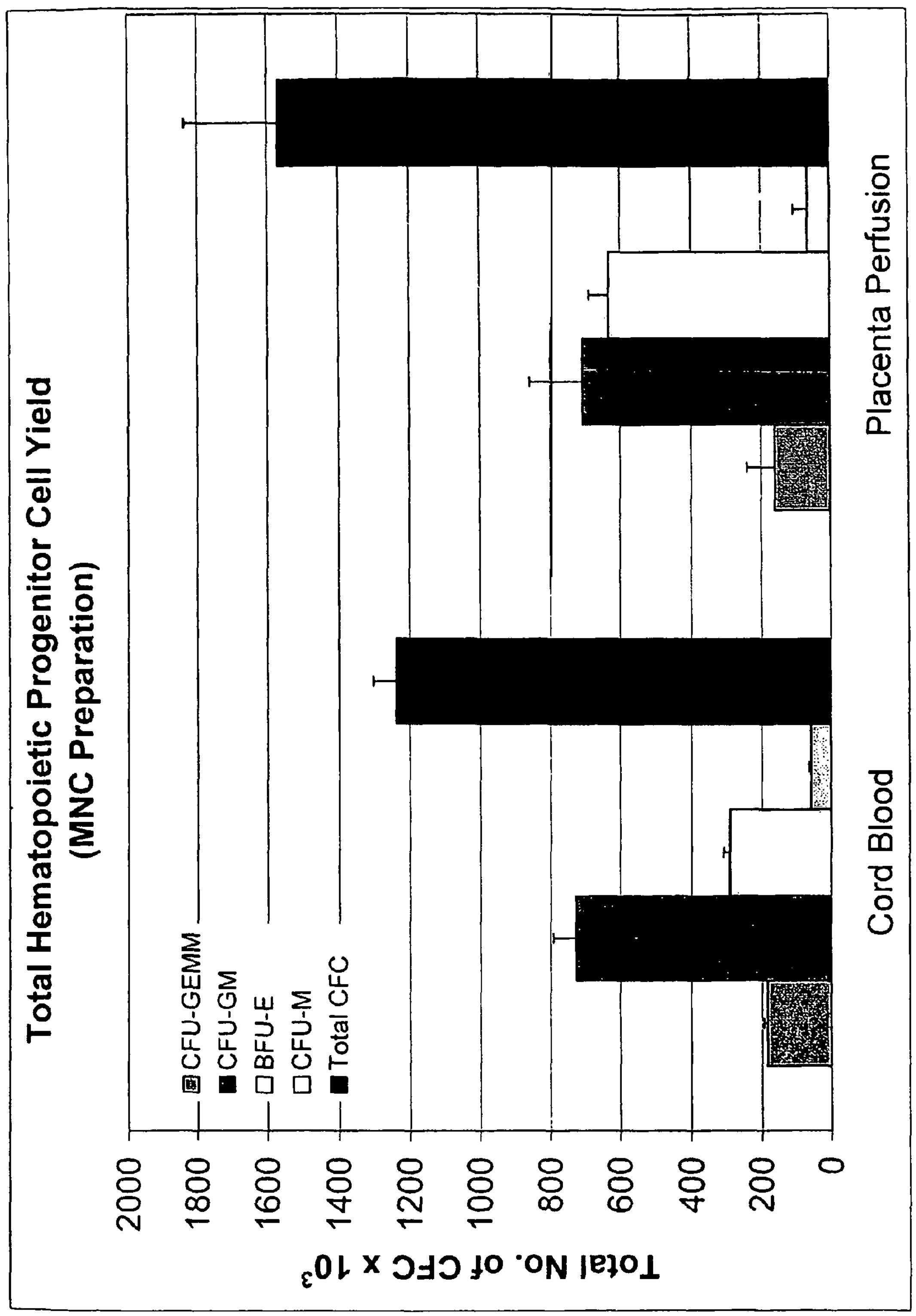
FIG. 4C is a graph of total amount of progenitor cells present in a syringe cord blood sample and the perfusate with respect to mononuclear cells.

Table 5C and FIG. 4C illustrate the total amount of progenitor cells present in the syringe cord blood sample and the perfusate with respect to mononuclear cells. As shown below, the syringe sample contained more CFU-GEMM and CFU-GM cells than the perfusate, while the perfusate contained more BFU-E and CFU-M cells that the cord blood sample.

TABLE 5C

| Total Progenitor Cell Yield × $10^3$ (Mononuclear Cell Preparation) | | | | |
|---|---|---|---|---|
| Colony Type | Cord Blood | Placenta Perfusion | SD1 | SD2 |
| CFU-GEMM | 183.9 | 159.6 | 10.17 | 81.2 |
| CFU-GM | 728.7 | 709.24 | 63.624 | 150.36 |
| CFU-E | 293.01 | 632.8 | 16.773 | 56.56 |
| CFU-M | 57.84 | 64.4 | 6.594 | 42 |
| Total CFC | 1237.78 | 1568 | 64.779 | 268.8 |

Figure 4D:
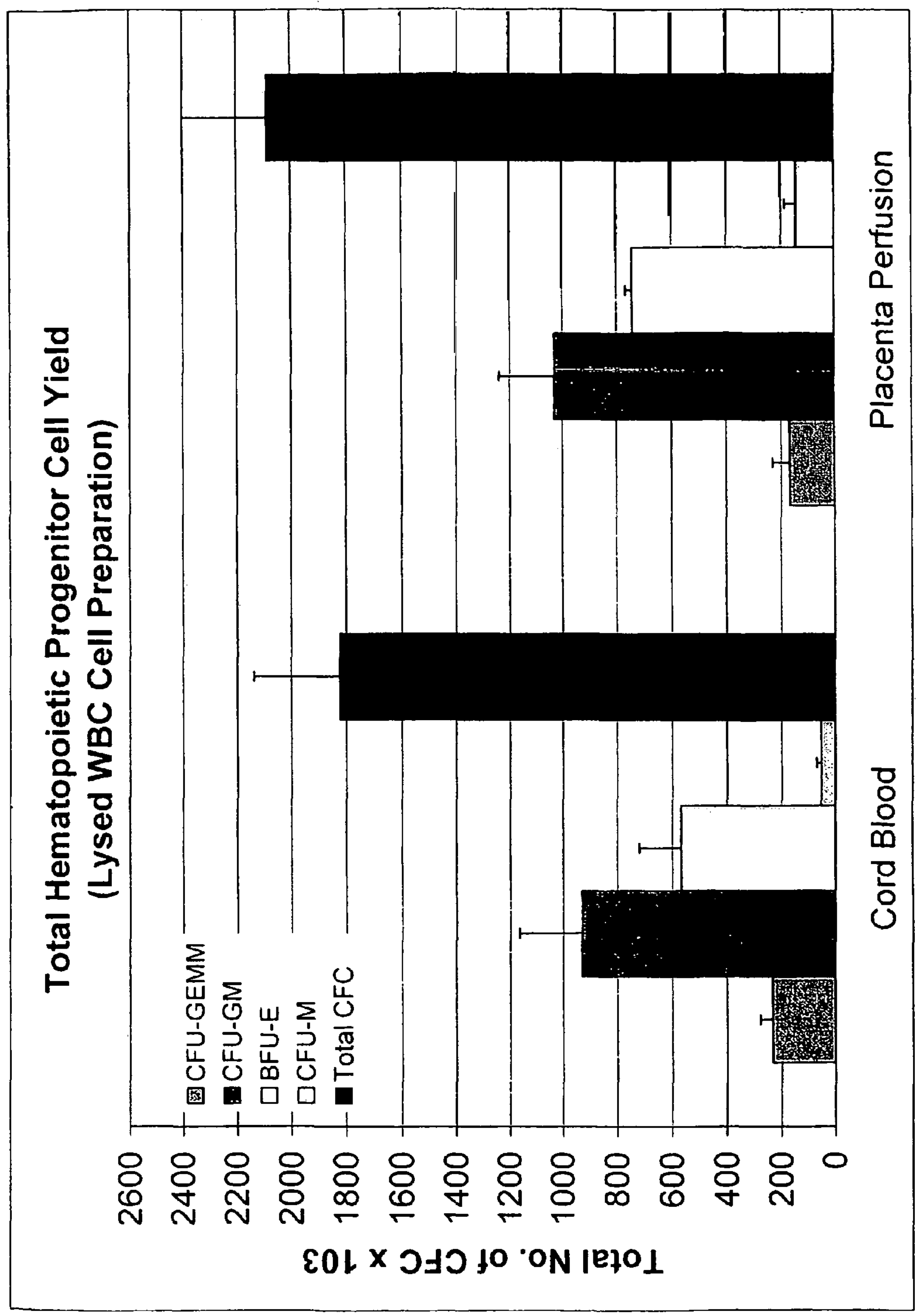
FIG. 4D is a graph of total amount of progenitor cells present in the syringe cord blood sample and the perfusate with respect to lysed white blood cells.

Table 5D and FIG. 4D illustrate the total amount of progenitor cells present in the syringe cord blood sample and the perfusate with respect to lysed white blood cells. As shown below, the syringe sample contained more CFU-GEMM and CFU-GM cells than the perfusate, while the perfusate contained more BFU-E and CFU-M cells that the syringe cord blood sample.

TABLE 5D

| Total Progenitor Cell Yield × $10^3$ (Lysed Total White Blood Cell Preparation) | | | | |
|---|---|---|---|---|
| Colony Type | Cord Blood | Placenta Perfusion | SD1 | SD2 |
| CFU-GEMM | 234.24 | 167.76 | 44.896 | 63.36 |
| CFU-GM | 929.152 | 1029.6 | 236.192 | 208.8 |
| CFU-E | 566.08 | 741.6 | 152.256 | 23.7 |
| CFU-M | 52.704 | 144 | 17.177 | 41.76 |
| Total CFC | 1821.801 | 2088 | 316.224 | 313.92 |

Figure 5:
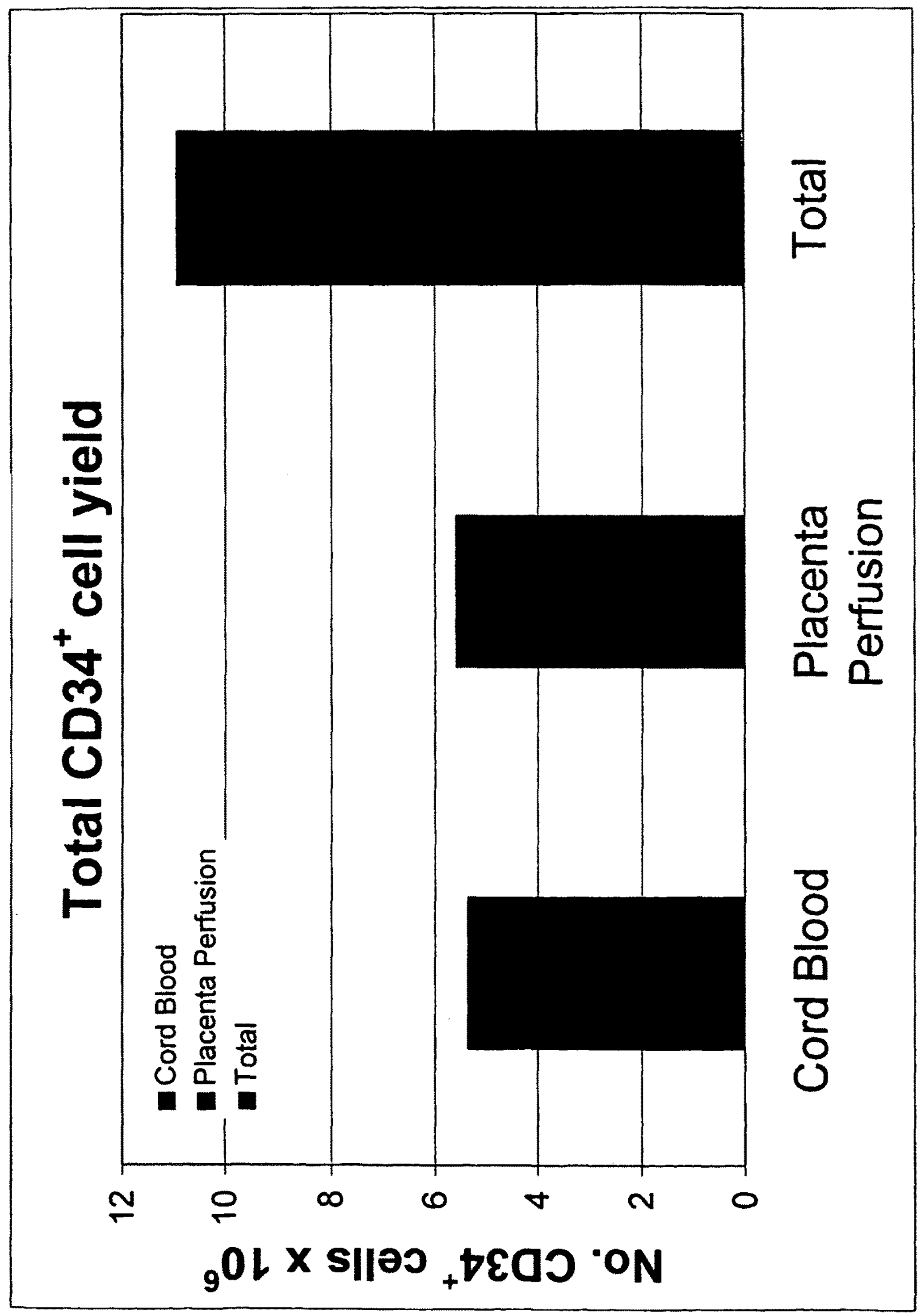
FIG. 5 is a graph of total CD34+ cell yield and also by attribution to the cord blood sample and cells extracted by placenta perfusion according to the method of the present invention.

There is no need to take a syringe sample of cord blood prior to a clinical pulsatile perfusion. It is believed a clinical pulsatile perfusion will also extract substantially all those cells which were extracted by syringe in the application examples. Table 6 and FIG. 5 illustrate that, in a routine procedure in which a clinician does not extract cells from the umbilical cord by syringe, one can expect to extract approximately $10.96\times10^6$ cells by perfusion of the placenta and umbilical cord.

TABLE 6

| Total Number of CD34+ Cells × $10^6$ | | | |
|---|---|---|---|
| | Cord Blood Syringe Sample | Placenta Perfusion | Total |
| MNC Preparation | 5.368 | 5.6 | 10.96 |

The present invention provides a method for the non-controversial production of non-embryonic, pluripotent stem cells in significant amounts. More particularly, the method can remove 90% or greater of the stem cell colonies from the placenta/umbilical cord, with 90% or greater purity. These cells can be used as is, or can be cultured and grown into cell lines. Applications include both pediatric and adult non-related bone marrow recipients, trauma patient recovery care; reconstructive surgeries such as removing wrinkles, breast enlargements and reductions, and other reconstructive surgeries where minimum scarring is permissible, vaccine development, and research generally, including research directed to curing Alzheimers', Parkinson's, and diabetes. These cells may also be used for the regeneration of nerve tissue, and development of new organs.

The present subject matter has been illustrated in great detail by the above specific Examples. It is to be understood that these Examples are illustrative embodiments and that the described subject matter is not to be limited by any of the Examples or details in the Description. Those skilled in the art will recognize that the described subject matter is capable of many modifications and variations without departing from the scope thereof. Accordingly, the Detailed Description and Examples are meant to be illustrative and are not meant to limit in any manner the scope of the subject matter as set forth in the following claims. Rather, the claims appended hereto are to be construed broadly within the scope and spirit of the described subject matter.

I claim:

1. A method for extracting stem cells from a human non-embryonic stem cell source, comprising:

providing an isolated human non-embryonic stem cell source comprising stem cells;

perfusing the human non-embryonic stem cell source with a rhythmic, intermittent flow of a perfusion solution through the stem cell source in a manner whereby said flow is pulsed to simulate an in vivo human pulse rate to produce a perfusate comprising stem cells and a perfused non-embryonic stem cell source; and isolating the stem cells from the perfusate to produce isolated stem cells.

2. The method of claim 1, wherein perfusing comprises first placing the human non-embryonic stem cell source into a perfusion circuit of a pulsatile perfusion machine; and operating the pulsatile perfusion machine to perfuse the human non-embryonic stem cell source with a rhythmic, intermittent flow of perfusion solution through the stem cell source under conditions sufficient to produce a perfusate comprising stem cells.

3. The method of claim 1, wherein the human non-embryonic stem cell source comprises one or more members selected from the group consisting of human placenta and human umbilical cord.

4. The method of claim 2, further comprising prior to first placing, priming the pulsatile perfusion machine with a priming solution.

5. The method of claim 4, wherein the priming solution comprises the perfusion solution.

6. The method of claim 1, wherein the flow is pulsed at a pulse rate of from 60 beats per minute to 80 beats per minute.

7. The method of claim 1, wherein the human stem cell source is a non-exsanguinated stem cell source.

8. The method of claim 3, wherein the method extracts placental blood, cord blood or both placental and cord blood from the human stem cell source.

* * * * *